(12) United States Patent
Bernhardt et al.

(10) Patent No.: US 8,718,342 B2
(45) Date of Patent: May 6, 2014

(54) METHOD AND DATA-PROCESSING SYSTEM FOR DETERMINING THE PROPORTION OF CALCIUM IN CORONARY ARTERIES

(75) Inventors: Dominik Bernhardt, Karlsruhe (DE);
Jörg Hausleiter, München (DE);
Carsten Thierfelder, Pinzberg (DE);
Johann Uebler, Nürnberg (DE);
Fernando Vega-Higuera, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 916 days.

(21) Appl. No.: 12/729,267

(22) Filed: Mar. 23, 2010

(65) Prior Publication Data
US 2010/0260400 A1    Oct. 14, 2010

(30) Foreign Application Priority Data
Mar. 25, 2009    (DE) .......................... 10 2009 014 763

(51) Int. Cl.
*G06K 9/00*    (2006.01)

(52) U.S. Cl.
USPC ............................................. 382/131

(58) Field of Classification Search
None
See application file for complete search history.

(56) References Cited

U.S. PATENT DOCUMENTS

| | | | |
|---|---|---|---|
| 6,847,040 B2 * | 1/2005 | Strommer ................ | 250/370.09 |
| 6,947,040 B2 | 9/2005 | Comaniciu et al. | |
| 7,907,766 B2 * | 3/2011 | Lehel et al. .................... | 382/131 |
| 7,940,970 B2 * | 5/2011 | Levanon et al. ............. | 382/128 |
| 7,983,459 B2 * | 7/2011 | Begelman et al. ............ | 382/128 |
| 2005/0228254 A1 * | 10/2005 | Torp et al. ..................... | 600/407 |
| 2006/0064007 A1 | 3/2006 | Comaniciu et al. | |
| 2007/0248261 A1 * | 10/2007 | Zhou et al. .................... | 382/154 |
| 2008/0159610 A1 * | 7/2008 | Haas et al. .................... | 382/131 |

(Continued)

FOREIGN PATENT DOCUMENTS

DE    102008003940 A1    7/2008

OTHER PUBLICATIONS

Agatston et al.; "Quantification of coronary artery calcium using ultrafast computed tomography"; Journal of American College of Cardiology, 1990, Vo. 15, pp. 827-832; Magazine; 1990; US.
Yoon et al. Coronary artery calcium: alternate methods for accurate and reproducible quantitation Acad Radiol. Oct. 1997;4(10):666-73; Others; 1997.

(Continued)

*Primary Examiner* — Nancy Bitar
(74) *Attorney, Agent, or Firm* — Harness, Dickey & Pierce

(57) ABSTRACT

A method and a data-processing system are disclosed for determining the proportion of calcium in coronary arteries using image data from CT angiography. In at least one embodiment of the method, anatomical landmarks are detected in the image data in the region of the heart and coronary arteries are segmented taking into account the detected landmarks. Regions with an increased HU value compared to a contrast agent surroundings are segmented in the segmented coronary arteries. A proportion of calcium respectively is calculated from the segmented regions for one or more of the segmented coronary arteries. At least the last two steps are carried out fully automatically by a data-processing system. Weighting factors for the individual regions are used when calculating the proportion of calcium, which weighting factors depend on both the threshold for segmenting the respective region and the volume of said region. The method and the data-processing system of at least one embodiment allow the dose exposure of the patient to be reduced and reduce the time expenditure of the user for determining the proportion of calcium.

10 Claims, 3 Drawing Sheets

(56) References Cited

U.S. PATENT DOCUMENTS

2008/0170763 A1* 7/2008 Begelman et al. ............ 382/128
2008/0219530 A1* 9/2008 Levanon et al. ............. 382/130
2013/0077872 A1* 3/2013 Kitamura .................... 382/203

OTHER PUBLICATIONS

Nasir et al. Ethnic differences between extra-coronary measures on cardiac computed tomography: multi-ethnic study of atherosclerosis (MESA). Atherosclerosis 2008;198(1):104-14.; Others; 2008.

* cited by examiner

METHOD AND DATA-PROCESSING SYSTEM FOR DETERMINING THE PROPORTION OF CALCIUM IN CORONARY ARTERIES

PRIORITY STATEMENT

The present application hereby claims priority under 35 U.S.C. §119 on German patent application number DE 10 2009 014 763.2 filed Mar. 25, 2009, the entire contents of which are hereby incorporated herein by reference.

FIELD

At least one embodiment of the present invention generally relates to a method and/or a data-processing system for determining the proportion of calcium in coronary arteries using image data from CT angiography.

BACKGROUND

Computed tomography (CT) provides a fast, noninvasive technique for obtaining slice images of the coronary arteries, from which the location and the extent of calcium deposits are evident. Commercially available data-processing programs afford the possibility of determining the proportion of calcium in the coronary arteries on the basis of the 3D image data or volume data from computed tomography. For this, a native CT scan is required initially, i.e. a record of 3D image data of the heart without a contrast agent. The user must then manually mark regions identified as calcium deposits in the various displays, which are later intended to contribute to quantifying the proportion of calcium. In general, the different coronary arteries are characterized by the user for this and labeled accordingly, for example using the conventional descriptors LM (left main), LAD (left anterior descending), LCX (left circumflexus) and RCA (right coronary artery). The proportions of calcium are then calculated in each case for the individual coronary arteries using the volumes of the marked regions.

The calculation is generally performed as a weighted sum of all pixels or voxels in the marked regions, which pixels or voxels lie above a threshold for the HU value, typically 130 HU. In the process, the weighting factor depends in each case on the maximum HU value within the region. This technique of weighting was originally introduced by Agatston and so the proportion of calcium determined thereby is also referred to as the Agatston score. After the native CT scan, a further CT scan may be performed under the administration of a contrast agent in such examinations in order to obtain a CT angiography record for a display with a high contrast.

Determining the proportion of calcium has previously been very complicated because the user had to view all individual images, identify the calcium deposits and mark them accordingly. On the one hand, this takes up a lot of time and, on the other hand, the reproducibility of the results depends strongly on the user. As a result of the two CT scans, the radiation dose to which the patient is exposed also increases.

SUMMARY

In at least one embodiment of the present invention, a method and/or a data-processing system are specified for determining the proportion of calcium in coronary arteries from CT image data, which can be performed with little complexity for the user and by way of which the dose can be reduced for the patient.

Only image data from CT angiography (CTA) is used in the proposed method of at least one embodiment for determining the proportion of calcium in the coronary arteries. In the 3D image data of the heart, anatomical landmarks are detected in the region of the heart for this purpose and coronary arteries, in particular the main vessels, are segmented taking into account the detected landmarks. Regions with an increased HU value compared to the contrast agent surroundings are segmented in the segmented coronary arteries. The proportion of calcium respectively is calculated from the segmented regions for one, more or all of the segmented coronary arteries and is output as a numerical value or illustrated graphically. At least the last two steps of segmenting the regions and calculating the proportion of calcium are carried out fully automatically, i.e. without user interaction, by a data-processing system.

On the one hand, this greatly reduces the complexity for the user in determining the proportion of calcium. On the other hand, the native CT scan, which previously was used predominantly for calculating the proportion of calcium, can be dispensed with. Rather, a CT angiography suffices when carrying out the present method of at least one embodiment and it can be used for both determining the proportion of calcium and examining pathologies on the coronary vessels. This can significantly reduce the radiation dose on the patient because, using the newest CTA techniques, the dose exposure of the CT angiography dependent on the figure of the patient is comparable to that of a native CT scan.

Furthermore, according to at least one embodiment of the invention, the proportion of calcium is calculated from the segmented regions using weighting factors for the individual regions which, unlike the prior art, do not depend on the maximum HU value within the region but on the threshold for the segmentation and on the volume of the segmented region. This is due to the different boundary conditions for segmenting CTA image data compared to image data obtained by a native CT scan. Thus, due to the contrast agent, a significantly higher threshold must be set for segmenting the regions than in the case of image data of the vessels without contrast agent. Therefore, during the segmentation, the determined proportions of calcium are lower than what is actually present because of the presence of the contrast agent. The weighting factors as a function of the threshold and the size of the segmented region at least approximately correct this undervaluation.

Determining the proportion of calcium not from the image data of a native CT scan but from CT angiography image data furthermore has the advantage that anatomical information in the image data can be used for segmenting the coronary arteries, which information allows automatic segmentation of these vessels with a high reliability. Thus, US 2006/0064007 A1 (the entire contents of which are hereby incorporated herein by reference) for example discloses a technique for automatically identifying anatomical landmarks in CTA image data of the heart, which technique is also preferably used in the present method first of all for determining suitable anatomical landmarks automatically for the subsequent segmentation of the coronary arteries. An automatic segmentation, as known from e.g. U.S. Pat. No. 6,947,040 B1 (the entire contents of which are hereby incorporated herein by reference), can then be performed on the basis of these landmarks, in which segmentation a ray propagation technique is used in the automatic segmentation. The disclosure content of both documents in respect of these techniques is included in the present patent application and the entire contents of both documents are hereby incorporated herein by reference.

The data-processing system preferably automatically determines in each case a point in the branches from the aorta to the two main coronary arteries (RCA and LM). The segmentation algorithm then uses these two points as initial points for segmenting these two coronary arteries.

In an example refinement of the method, a point in the aorta is likewise determined to be a landmark automatically, preferably a point in a central region of the aorta. This can also be carried out by the data-processing system using the previously explained technique. This point in the aorta determined in advance is then used as a comparison value in the subsequent segmentation of the regions with proportions of calcium in order to set a threshold above the HU value of the contrast agent for segmenting the regions enriched with calcium. Herein, a difference value of how much the threshold is higher than the comparison value can be prescribed. This comparison value avoids an overlap of the segmentation into areas filled with contrast agent in disadvantageous circumstances during the automatic segmentation of the regions.

A two-dimensional table which can be accessed by the data-processing system during the calculation is preferably provided for automatic calculation of the proportion of calcium, in which table the weighting factors to be applied have been stored. This table specifies the respective weighting factors for a multiplicity of combinations of thresholds and sizes of regions.

In a development of at least one embodiment of the method, the segmented coronary arteries are also identified and appropriately characterized or labeled. The can be brought about either by the user or in a fully automatic fashion. The fully automatic identification and labeling is preferably carried out by an automatic analysis of the spatial location of these coronary arteries.

Thus, for example, the region of the image data used by the coronary arteries can be subdivided into subregions for the analysis, which subregions are each assigned a characterization or a label. Known statistical assumptions relating to the spatial location of the coronary arteries on the heart are used for the subdivision of the volume of the data record and the assignment of the label. The subregion in which the majority of this coronary artery is situated is then determined for each segmented coronary artery. The coronary artery then obtains the characterization or label assigned to this subregion.

The data-processing system designed for carrying out at least one embodiment of the method requires, in a known fashion, corresponding interfaces for accessing the 3D image data, storage and a mathematical processor. This data-processing system is preferably connected to an image display unit, by which the slice images from the 3D image data or a 3D visualization of the image data and the result of determining the proportion of calcium can be displayed. The data-processing system comprises a determination module in the form of a software program designed for executing the method steps of at least one embodiment of the proposed method.

BRIEF DESCRIPTION OF THE DRAWINGS

In the following text, the proposed method will once again be explained briefly on the basis of an example embodiment in conjunction with the drawings, in which.

DETAILED DESCRIPTION OF THE EXAMPLE EMBODIMENTS

Figure 1:
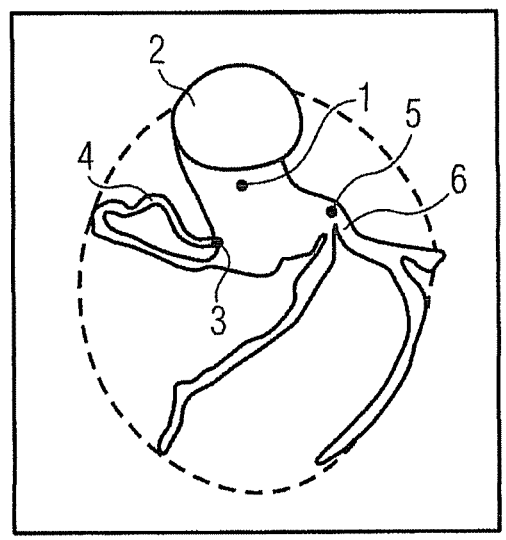
FIG. 1 shows a display of CTA image data of the heart with marked anatomical landmarks.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 6:
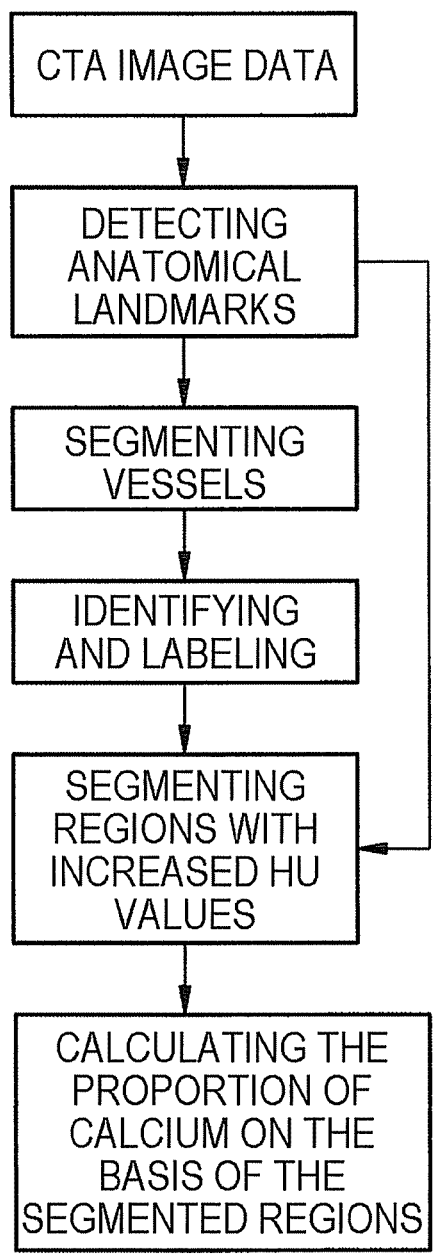
FIG. 6 shows a schematic illustration of the individual method steps of an embodiment of the proposed method.

In the following text, the proposed method will once again be explained briefly on the basis of an example embodiment in conjunction with the drawings. Here, the method procedure of an example embodiment, with the individual method steps, is sketched in FIG. 6.

In the present example, the data-processing system initially detects and marks important anatomical landmarks automatically in the CTA image data of the heart. A technique as disclosed in US 2006/0064007 A1 is used for this. A central point 1 in the aorta 2 and respectively one central point 3 of the branch point or opening to the right main coronary artery (RCA 4) and one central point 5 in the branch point or opening to the left main coronary artery (LM 6) are marked as anatomical landmarks. These two central points 3, 5 in the branch points are used as initial points for the subsequent automatic segmentation of the coronary arteries with the aid of a ray propagation technique as per U.S. Pat. No. 6,974,040 B1. For this, FIG. 1 shows a simplified display of the 3D image data with the detected and marked points 1, 3, 5.

Figure 2:
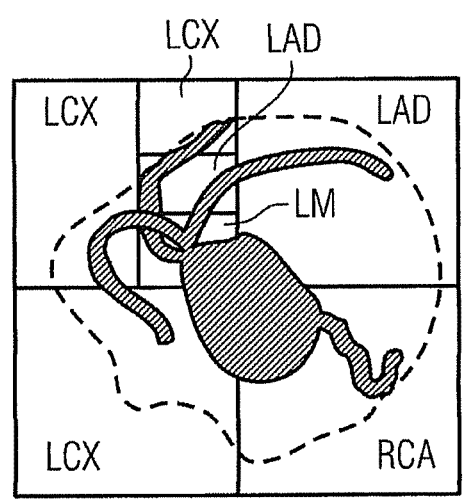
FIG. 2 shows a schematic illustration of the subdivision of the image data into subregions.

After automatically segmenting the coronary arteries, the latter are identified and labeled accordingly. This is performed on the basis of an analysis of the spatial location of the segmented vessels. The usual abbreviations LM, LAD, RCA and LCX are used as labels. For the purpose of automatic identification, the region in the image data taken up by the segmented vessel tree is subdivided into geometric subregions, which are respectively assigned one label. The subdivision and label are brought about by way of corresponding statistically correct assumptions about the shape of the vessel structures around the heart. Thus, for example, the region on the right side of the heart is usually crossed by the RCA. If a segmented vessel mainly runs in this region assigned the label RCA, the corresponding vessel likewise is provided with the label RCA. The same steps are performed with the remaining segmented vessels. Subsequently, the vessel segment from which the vessels labeled as LAD and LCX branch off at a common branch point is labeled LM. For this, FIG. 2 schematically shows a selected subdivision into individual subregions and the labeling thereof in an example slice plane through the 3D image data.

Segmenting the most important coronary arteries and the labeling thereof is followed by the automatic detection and segmentation of regions in these vessels that contain calcium deposits. For this, cross-sectional images through these vessels are analyzed locally in a statistical fashion. Here, the cross-sectional images are generated at regular intervals from the 3D image data, preferably perpendicularly to the axis of the vessel. In the respective sectional images, an irregular increase in the HU values, or the brightness values correlated therewith, above the HU values or brightness values of the contrast agent is sought after. If such a region is found, a seed point is automatically placed within this region and the region is automatically segmented in the 3D image data using a thresholding technique. A value above the HU value or brightness value of the surrounding contrast agent is selected as a threshold.

Figure 3:
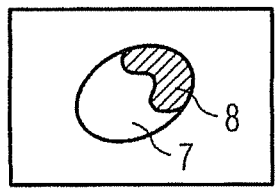
FIG. 3 shows a slice image through a vessel in which calcium deposits can be seen.

Preferably, the previously determined point in the aorta is used as a comparison value for this, wherein the threshold in this case is set at a suitable value above this comparison value. Preferably, thresholds are resorted to that are plotted in a diagram against the respectively applicable comparison value in the aorta, with a regression curve being plotted in this diagram, and that previously were manually selected by medical practitioners in a multiplicity of different (earlier) cases. In the present method, this regression curve can then be used to automatically determine the threshold as a function of the calculated comparison value in the aorta. This can avoid an undesired overlap of the segmentation into regions within the vessel that are filled with contrast agent. The procedure is performed for all segmented vessels in order to obtain all regions with calcium deposits in these vessels for the subsequent calculation of the proportion of calcium. For this, FIG. 3 shows an example slice image through a coronary artery 7, in which a region 8 with calcium deposits can be seen due to the increased HU value or brightness value compared to the contrast agent.

Figure 4:
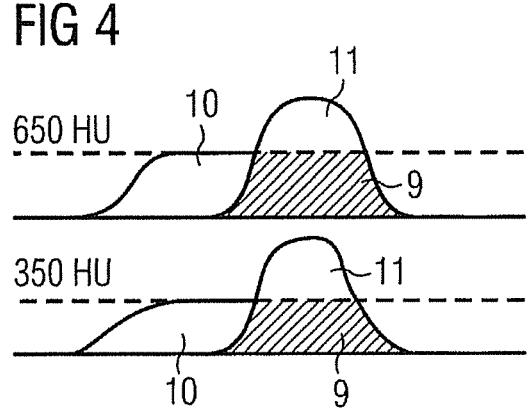
FIG. 4 shows a schematic illustration for demonstrating the calcium regions covered by the contrast agent.

As was previously explained above, the boundary conditions for segmentation in CTA image data differ from those in CT image data of a native CT scan. FIG. 4 uses two examples containing different amounts of contrast agent and with differently sized regions of the calcium deposit to show the conditions when segmenting the CTA image data. The threshold used for segmenting depends strongly on the contrast agent amount within the vessel and so different thresholds, which respectively have to lie above the HU value for the contrast agent in the vessel, are required for different amounts. In addition, the ratio of the non-segmented voxels within the calcium deposits—due to the higher threshold—and the correctly segmented voxels also strongly depends on the size of the region. In FIG. 4, calcium deposits not registered whilst segmenting are indicated by the shaded region 9. The contrast agent is denoted by reference sign 10 and the registered calcium deposits are denoted by reference sign 11.

Figure 5:
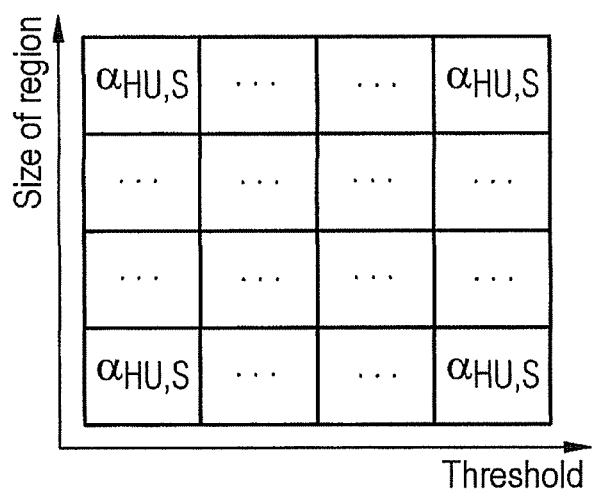
FIG. 5 shows an example of a table with weighting factors.

So that the subsequently determined proportion of calcium is not falsified by these conditions, the individual segmented regions are provided with correction or weighting factors, which take these conditions into account. According to the invention, the weighting factors used here depend on the threshold for the segmentation and the size of the segmented region. The weighting factor has to increase with an increasing threshold. The same holds true for the size of the region. In the present example, a two-dimensional correction table is used for this purpose, in which the X- and the Y-coordinates respectively correspond to the threshold and the size of the region. Since the threshold is set automatically and the size of the respective region is determined in the proposed method, a suitable weighting factor can be obtained by resorting to the stored correction table. For this, FIG. 5 shows the structure of such a correction table with the weighting factors a in an example fashion.

By using the proposed method, a native CT scan can be dispensed with and so the dose exposure of the patient is reduced. A simple low-dose CTA scan suffices to allow the reliable determination of the proportion of calcium. Furthermore, the proportions of calcium can be determined in a semi- or fully automatic fashion from the 3D image data and so the time expenditure of the user is reduced and a better reproducibility of the results is achieved.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining the proportion of calcium in coronary arteries using image data of a heart from CT angiography, comprising:
    detecting anatomical landmarks in an image data in the region of the heart and segmenting the coronary arteries, taking into account the detected anatomical landmarks;
    identifying and labeling the segmented coronary arteries based on an analysis of a spatial location of the segmented coronary arteries, the analysis including dividing a region into subregions and assigning a label to each of the subregions based on statistical assumptions relating to the spatial location of the coronary arteries, wherein segmented coronary arteries that mainly run in one of the subregions obtain the label assigned to the one of the subregions;
    segmenting regions with an increased HU- or brightness value, compared to a contrast agent surroundings, in the segmented coronary arteries; and
    calculating a proportion of calcium from respective segmented regions for one or more of the segmented coronary arteries, wherein
    at least the segmenting and calculating are carried out fully automatically by a data-processing system, and weighting factors for the individual regions are used when calculating the proportion of calcium, the weighting factors depending on both a threshold for the segmenting of a respective region and a volume of the respective region.

2. The method as claimed in claim 1, wherein the detecting the anatomical landmarks at least comprises localizing one point of an aorta of the heart.

3. The method as claimed in claim 2, wherein an HU- or brightness value at a localized point in the aorta is used as a comparison value for segmenting the regions in order to avoid an overlap of the segmentation into areas filled with contrast agent.

4. The method as claimed in claim 1, wherein a two-dimensional table is provided, in which the weighting factors are recorded as a function of the threshold and the volume.

5. The method as claimed in claim 1, wherein the detecting of the anatomical landmarks comprises respectively localizing points in branches from an aorta of the heart to two main coronary arteries of the heart.

6. The method as claimed in claim 5, wherein the two main coronary arteries are segmented automatically using an algorithm operating on the basis of a ray propagation technique, and the localized points in the branch points form initial points for the segmentation.

7. The method as claimed in claim 1, wherein all of the detecting, identifying and labeling, segmenting regions and calculating are carried out fully automatically by a data-processing system.

8. A data-processing system for determining a proportion of calcium in coronary arteries using image data from CT angiography, designed for executing the method as claimed in claim 1.

9. A data-processing system for determining the proportion of calcium in coronary arteries using image data of a heart from CT angiography, comprising:

a device configured to detect anatomical landmarks in the image data in a region of the heart and segmenting the coronary arteries, taking into account the detected anatomical landmarks;

a data processing system configured to, identify and label the segmented coronary arteries based on an analysis of a spatial location of the segmented coronary arteries, the analysis including dividing a region into subregions and assigning a label to each of the subregions based on statistical assumptions relating to the spatial location of the coronary arteries, wherein segmented coronary arteries that mainly run in one of the subregions obtain the label assigned to the one of the subregions, segment regions with an increased HU- or brightness value, compared to a contrast agent surroundings, in the segmented coronary arteries, and calculate a proportion of calcium from respective segmented regions for one or more of the segmented coronary arteries, wherein at least the segmenting and calculating are carried out fully automatically, and weighting factors for the individual regions are used when calculating the proportion of calcium, the weighting factors depending on both a threshold for the segmenting of a respective region and a volume of the respective region.

10. A non-transitory computer readable medium including program segments for, when executed on a computer device, causing the computer device to implement the method of claim 1.

* * * * *